United States Patent [19]

Yamasaki

[11] Patent Number: 5,342,770
[45] Date of Patent: Aug. 30, 1994

[54] CONJUGATE INCLUDING A SUGAR AND PEPTIDE LINKER

[75] Inventor: Nobuyuki Yamasaki, Fukuokaken, Japan

[73] Assignee: Chisso Corporation, Osaka, Japan

[21] Appl. No.: 60,038

[22] Filed: May 11, 1993

Related U.S. Application Data

[63] Continuation of Ser. No. 568,062, Aug. 16, 1990, abandoned.

[30] Foreign Application Priority Data

Aug. 25, 1989 [JP] Japan .................. 218885

[51] Int. Cl.$^5$ ............ C12N 11/10; C12N 11/02; C07K 17/10
[52] U.S. Cl. .................. 435/178; 435/177; 435/181; 530/402; 530/403; 530/406; 530/813; 530/816
[58] Field of Search ............ 435/177, 178, 181; 530/402, 403, 406, 813, 816

[56] References Cited

U.S. PATENT DOCUMENTS

| | | | |
|---|---|---|---|
| 4,055,635 | 10/1977 | Green et al. | 435/180 |
| 4,094,744 | 6/1978 | Hartdegen et al | 435/182 |
| 4,401,647 | 8/1983 | Krohn et al. | 424/1.1 |
| 4,496,689 | 1/1985 | Mitra | 435/178 |
| 4,585,754 | 4/1986 | Meisner et al. | 435/178 |
| 4,659,569 | 4/1987 | Mitsuhashi et al. | 424/89 |
| 4,867,973 | 9/1989 | Goers et al. | 424/85.91 |
| 5,006,333 | 4/1991 | Saifer et al. | 424/78 |
| 5,037,883 | 8/1991 | Kopecek et al. | 525/54.1 |

FOREIGN PATENT DOCUMENTS 0363874 10/1990 European Pat. Off. ............ 435/178

OTHER PUBLICATIONS

Stryer (1975) "Biochemistry", 2nd Ed., Freeman & Co., San Francisco, p. 774.

Primary Examiner—Douglas W. Robinson
Assistant Examiner—Jon P. Weber
Attorney, Agent, or Firm—Leydig, Voit & Mayer

[57] ABSTRACT

The present invention provides a conjugate in essentially pure form comprising a sugar linked to a protein through a peptide linker, wherein said sugar has a reducing terminal and is free of carboxyl groups, and wherein the reducing terminal of said sugar is linked to the peptide linker. The present invention further provides a conjugate in essentially pure form comprising a sugar linked to an enzyme through a peptide linker, wherein said sugar has a reducing terminal and is free of carboxyl groups, and wherein the reducing terminal of said sugar is linked to the peptide linker. The present invention additionally provides a conjugate in essentially pure form comprising a sugar linked to lysozyme through a peptide linker, wherein said sugar has a reducing terminal and is free of carboxyl groups, and wherein the reducing terminal of said sugar is linked to the peptide linker.

16 Claims, 2 Drawing Sheets

CONJUGATE INCLUDING A SUGAR AND PEPTIDE LINKER

This application is a continuation of application Ser. No. 07/568,062, filed Aug. 16, 1990, now abandoned.

BACKGROUND OF THE INVENTION

1. Field of the Invention

This invention relates to a hybrid, which has a sugar having a reducing terminal and containing no carboxyl group bound with lysozyme through a peptide linkage and a process for producing the same, and the object is to enhance the stability of lysozyme. Further, another object is to provide an activated sugar which is a sugar having a reducing terminal and containing no carboxyl group bound with N-hydroxysuccinimide through a peptide linkage which activated sugar is necessary to produce the above sugar-lysozyme hybrid, and a process for producing the activated sugar.

2. Description of Related Art

Proteins are constituted by a primary structure formed by linking 20 kinds of amino acids and a steric structure defined by the above primary structure. It has already been known that proteins have various functions, and even proteins stable in vivo become unstable when used in vitro.

When superior functions of proteins are applied to various uses, proteins have the following drawbacks:

① they are unstable to heat, alkalies and acids and liable to be denatured;
② they are insoluble in organic solvents and liable to lose their activity;
③ they have antigenic properties; etc.

In order to overcome these drawbacks, proteins have been chemically modified. Such chemical modification of proteins into a protein hybrid has made it possible to compensate the above drawbacks. Various processes have been proposed for such chemical modification. Among these processes, the most often employed one is a process of using as a modifying agent, a polyethylene glycol (hereinafter abbreviated to PEG) which is a non-immunity synthetic high-molecular weight compound.

According to the above process, as illustrated below in the equations, a synthesized substance (an activated PEG) is prepared from monomethoxypolyethylene glycol and a cyanuric chloride (2,4,6-trichloro-S-triazine), followed by reacting this activated PEG with a protein to produce a PEG-protein hybrid.

Utilizing this protein-hybrid, various application examples, as shown below, have been reported, but practical commercially employed examples appear to be few. This is because the activated PEG is unstable; no product having uniform properties is obtained; cyanuric chloride raises a tohieity problem; the reaction of the activated PEG with proteins does not occur quantitatively and smoothly; etc.

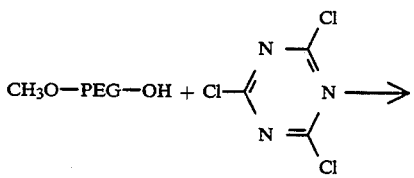

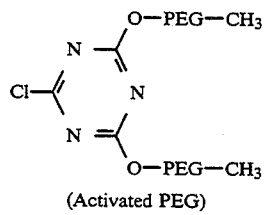
(Activated PEG)

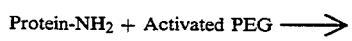
Protein-NH₂ + Activated PEG ⟶

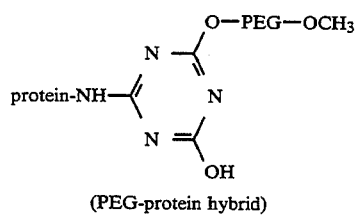
(PEG-protein hybrid)

The application examples of PEG-protein hybrid are shown below.

(1) PEG-asparaginase (T. Pharmac., Y. Kamisaki et al; Exp. Therap. 216, 410).

This hybrid prolongs the half-life period in blood of asparaginase as an antitumor enzyme and reduces its antigenic properties.

(2) By utilizing a PEG-enzyme hybrid, enzyme reactions have been made possible even in organic solvents (Y. Imada et al; Trends in Biotechnology 4 190(1986), K. Takahashi et al; J.Org Chem 50 3414(1985) K. Takahashi et al; Enzyme 32 235 (1984) K.Takahashi et al; Bioch em Biophys Res. Commun:125 761(1984)). Catalase, lipase, chymotrypsin, peroxidase, etc.

(3) PEG-adenosine deaminase (M.S. Hershfield et al; N. Engl. J. Mol. 316,493 (1985))

Among genetic enzyme-deficient phenomena, there is adenosine aminase (ADA)-deficient phenomenon. When this ADA is administered, if it is made up into PEG-ADA hybrid, it has been reported that this hybrid has effects of notably prolonging the half-life period in blood, etc.

(4) PEG-interleukin 2 (Taiji Imoto; Chemistry and Organism, Vol. 27, page 426, 1989)

Interleukin 2 which is a kind of lymphokines has been mass-produced according to recombinant DNA technique, but it is deficient in a sugar chain so that it is unstable, but when it is made up into PEG-interleukin 2 hybrid, it could have been stabilized and also its antitumor effect could have been improved.

In order to make up a hybrid with proteins, sugars have been also utilized besides PEG. As processes utilizing sugars, there are the following processes (i) to (iv), and the effects of the resulting hybrids are almost the same as those in the case of PEG:

(i) Periodic acid oxidation process:

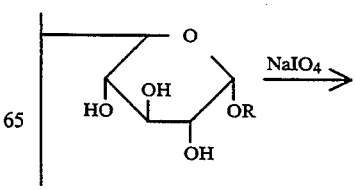

-continued

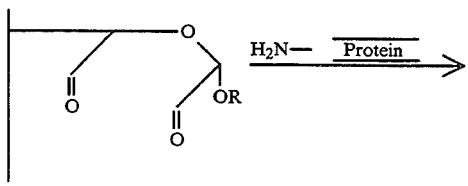

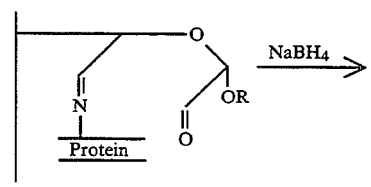

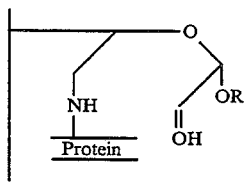

(ii) Bromine cyanide process

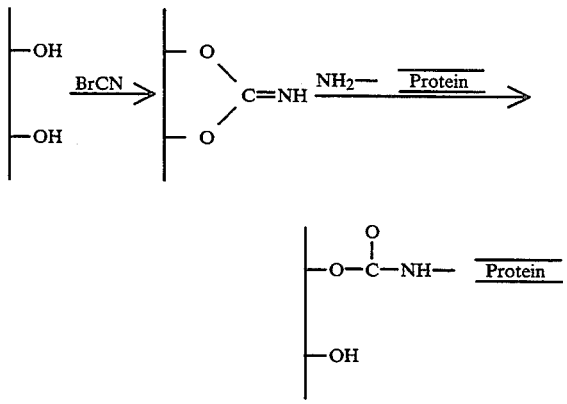

(iii) Cyanuric chloride process

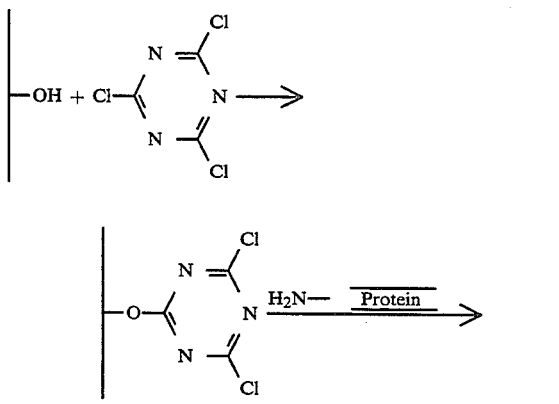

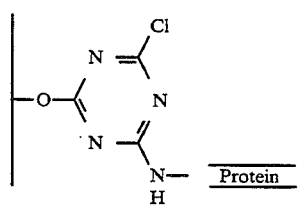

-continued (iv) Epichlorohydrin process

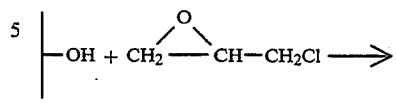

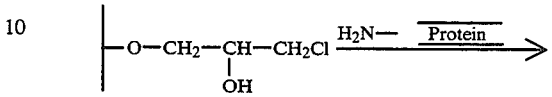

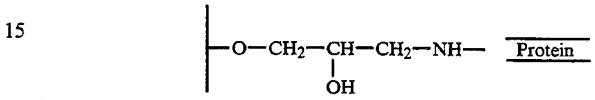

The process (i) has drawbacks that the reaction with periodic acid is so severe that sugars are often decomposed; binding with proteins requires the use of a reducing agent; there is a possibility that proteins are denatured; etc.

The process (ii) has drawbacks that poisonous bromine cyanide is used; when proteins are bound, it is necessary to severely adjust the pH in the process; etc.

The process (iii) has drawbacks that cyanuric chloride is poisonous; the reaction of cyanuric acid with sugars does not progress smoothly.

The process (iv) has drawbacks that sugars crosslink with each other due to epichlorohydrin; etc. The drawbacks common to these processes consist in that since the above respective substances react with —OH of the constituting sugars, the binding position is indefinite and also since they react with any —OH of sugars, the properties specific to the respective sugars are lost.

Lysozyme as a bacteriolytic enzyme has been broadly used for medical industry, etc., and in order to enhance its stability, high-level techniques are required or cumbersome operations are required; for example, the composition of constituting amino acids varies according to the gene engineering technique used; crosslinking is carried out between the objective amino acids (see, Taiji Imoto; Chemistry and Organism, Vol. 27, page 426, 1989).

SUMMARY OF THE INVENTION

The present invention has the following three main objects:

(1) An object is to provide an activated sugar useful for reacting a sugar having a reducing terminal and containing no carboxyl group with the amino group of a protein only at the reducing terminal of the sugar, without using any poisonous reagent, to thereby smoothly effect the reaction of combining the sugar with the protein, without losing the intrinsic properties of the sugar.

(2) Another object is to provide a hybrid of lysozyme with a sugar, utilizing the above activated sugar to thereby enhance the stability of lysozyme.

(3) A still further object is to provide processes for producing the above activated sugar and the above sugarlysozyme.

Other objects will be apparent from the description mentioned below.

The present invention has the following constitutions:

(1) A conjugate in essentially pure form comprising a sugar linked to a protein through a peptide linker, wherein said sugar has a reducing terminal and is free of carboxyl groups, and wherein the reducing terminal of said sugar is linked to the peptide linker.

(2) A hybrid according to item (1), wherein the sugar is amylose.

(3) A hybrid according to item (1), wherein the peptide is glycylglycine.

(3a) A conjugate in essentially pure form comprising a sugar linked to an enzyme through a peptide linker, wherein said sugar has a reducing terminal and is free of carboxyl groups, and wherein the reducing terminal of said sugar is linked to the peptide linker.

(3b) A conjugate in essentially pure form comprising a sugar linked to lysozyme through a peptide linker, wherein said sugar has a reducing terminal and is free of carboxyl groups, and wherein the reducing terminal of said sugar is linked to the peptide linker.

(4) A hybrid according to item (1), wherein the sugar is at least one member selected from the group consisting of monosaccharides, oligosaccharides and polysaccharides.

(5) An activated sugar which includes a sugar having a reducing terminal and containing no carboxyl group combined with N-hydroxysuccinimide, through a peptide linkage.

(6) An activated sugar according to item (5), wherein the peptide is glycylglycine.

(7) An activated sugar according to item (5), wherein the sugar is at least one men, her selected from the group consisting of monosaccharides, oligosaccharides and polysaccharides.

(8) A process for producing an activated sugar, which comprises reacting a sugar having a reducing terminal and containing no carboxyl group, with a peptide having an amino group and a carboxyl group at both the ends thereof in the presence of a reducing agent, followed by binding N-hydroxysuccinimide with the resulting material in the presence of a condensation agent.

(9) A process for producing an activated sugar according to item (8), wherein the peptide is glycylglycine.

(10) A process for producing an activated sugar according to item (8), wherein the sugar is at least one member selected from the group of monosaccharides, oligosaccharides and polysaccharides.

DETAILED DESCRIPTION OF PREFERRED EMBODIMENTS

Figure 1:
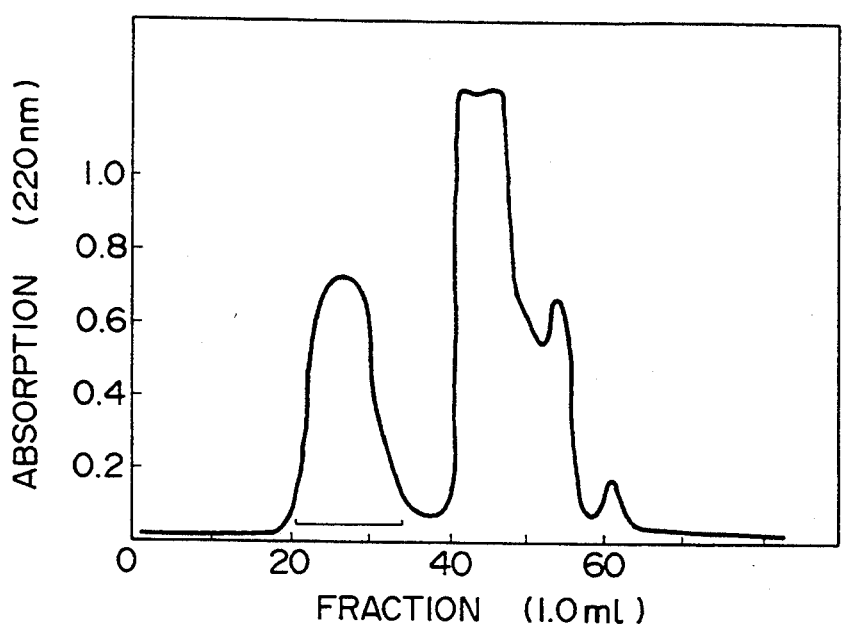
FIGS. 1 to 4 each show an explanatory chart illustrating examples of the present invention.

A. Preparation of Activated Sugar (1) First step:

A reducing sugar is dissolved in a buffer solution or an organic solvent such as dimethylsulfoxide, etc., followed by adding to the solution, a peptide having an amino group and a carboxyl group at the opposite the ends thereof and a reducing agent and reacting the mixture to prepare a compound as expressed by the formula (I) mentioned below.

The buffer solution in this case has no particular limitation, but it may contain no amino group and have a pH of 5 to 9. The sugar preferably includes monosaccharides, oligosaccharides or polysaccharides. The peptide has no particular limitation, but the number of the constituting amino acids is suitably 2 to 10. As the reducing agent, sodium borohydride (hereinafter abbreviated to SBH), sodium cyanoborohydride (NaBH3CN, hereinafter abbreviated to SCBH) and dimethylaminoborane ((CH3)2HNBH3, hereinafter abbreviated to DMAB) are preferred. The reaction temperature is preferably 10° to 60° C. After completion of the reaction, unreacted peptide and reducing agent are separated and removed by means of gel filtration or ultrafiltration membrane.

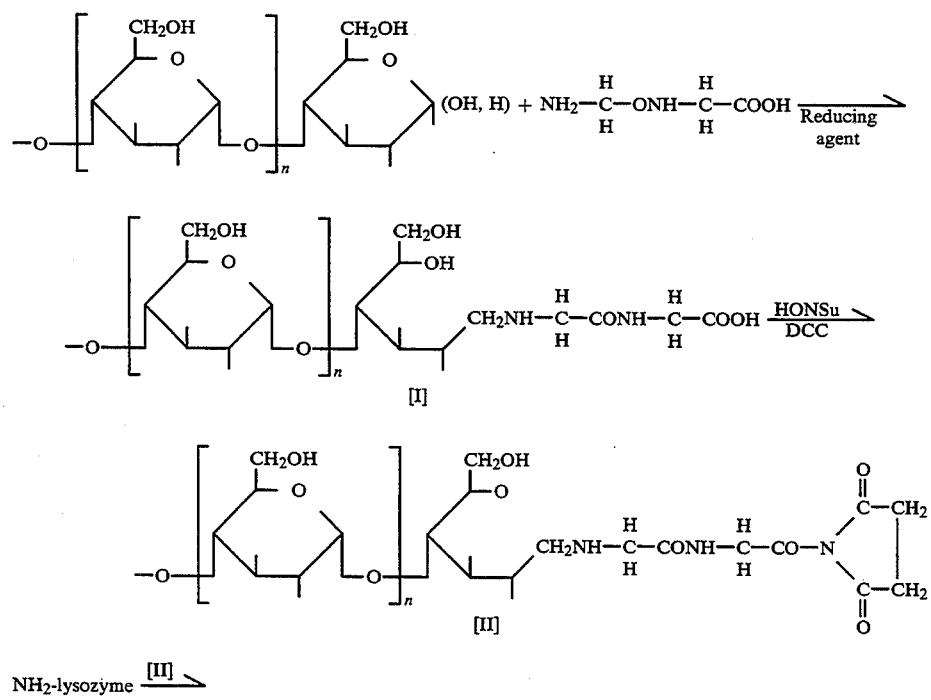

-continued

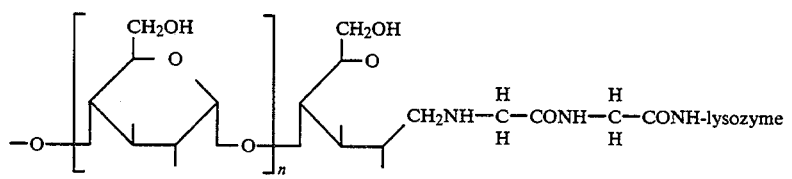

(2) Second step

The above compound of the formula (I) is dissolved in a buffer solution or an organic solvent, followed by adding to the solution, N-hydroxysuccinimide (hereinafter abbreviated to HONSu) and a condensation agent, to prepare a compound of the formula (II). The condensation agent is suitably dicyclohexylcarbodiimide (hereinafter abbreviated to DCC), 1-ethoxycarbonyl-2-ethoxy-1,2-dihydroxyquinoline (hereinafter abbreviated to EEDQ), disuccinimide carbonate (hereinafter abbreviated to DSC), 1-ethyl-3-(3-dimethylaminopropyl)-carbodiimide hydrochloride (hereinafter abbreviated to EDC), etc.

The compound of the formula (II) is a compound having a peptide sugar combined with HONSu and a novel compound so far not obtained and in a form readily reactive with the amino group of a protein (hereinafter referred to as activated sugar).

B. Preparation of Lysozyme-Sugar Hybrid

The activated sugar [II] is reacted with lysozyme in a buffer solution containing no amino group, followed by separating a sugar-lysozyme hybrid from the activated sugar [II] by means of gel filtration chromatography or an ultrafiltration membrane.

The above reaction progresses almost quantitatively, but in the case where unreacted lysozyme is present, it is possible to obtain a lysozyme-sugar hybridoma by separating lysozyme from the sugar-lysozyme hybrid by means of CM-ion exchanger as a cation exchanger.

As described above, according to the present invention, it is possible to obtain a lysozyme bound to the reducing terminal of the sugar-sugar hybrid in a comparatively simple manner. This is epoch-making. With proteins particularly enzymes other than lysozyme, too, it is possible to prepare a sugar-protein hybrid.

C. Stability of Sugar-Lysozyme Hybrid

In order to observe to what extent the stability of the sugar-lysozyme hybrid has been enhanced as compared with lysozyme alone, the activity of lysozyme subject to heat was examined. The activity of lysozyme was measured using glycol chitin as a substrate.

As a result, the activity of unmodified lysozyme was metably reduced at 80° C. or higher, whereas sugar-lysozyme hybrid could retain its activity as far as 80% even at high temperatures of 90° to 100° C.; hence such a high stability is epoch-making.

As the sugar, not only amylose but also aminopectine, chitosan, dextran, agarose, etc. are employed.

Sugars having carboxyl groups are undesirable to use in the present process since they cause intermolecular crosslinking of proteins with one another.

When pharmaceuticals of enzyme proteins are administered in a base form, the half-life period is so short that they are rapidly excreted from the kidney or decomposed so that the drug efficacy often cannot be obtained. The present invention is applied to achieving such increase in the stability of enzyme proteins in blood, an increase in the retention time thereof in blood, etc. In example described later, there will be described an increase in the retention time in blood, of superoxide dismutase (hereinafter abbreviated to SOD) which is an enzyme specifically decomposing the superoxide anion of active enzymes and having recently come to be used for removal of blood vessel obstacles in the brain and heart, Behcet's disease, etc.

The present invention will be described in more detail by way of examples, but it should not be construed to be limited thereto.

EXAMPLE 1

Preparation of Amylose-Glycylglycine

Amylose (weight average molecular weight: 29,000) (1.0 g) was dissolved in a 0.1 M phosphoric acid buffer (pH: 8.5) (10 ml), followed by adding glycylglycine in a quantity by mol of 5 times that of amylose and SCBH in a quantity by mol of 50 times that of amylose, agitating the mixture at 80° C. for 2 days, adjusting the pH to 3 with conc. hydrochloric acid, further agitating at 60° C. for 5 hours and adjusting the pH to 7 with N-NaOH.

The resulting reaction liquid is subjected to gel chromatography with a gel-filtering medium (Trademark: Cellulofine GCL-25) to remove unreacted glycylglycine SCBH. The gel filtration results are shown in FIG. 1. The first peak portion is separated. The subsequent peak is of glycylglycine SCBH. The separated liquid was freeze-dried. In addition, the gel filtration was carried out under conditions of column: 1.2×60 cm, eluent: water, and flow rate: 10 ml/hr. 0.9 g of amylose-glycylglycine was obtained.

EXAMPLE 2

Preparation of Activated Amylose

Amylose-glycylglycine (0.5 g) obtained in Example 1 was dissolved in dimethylsulfoxide (2 ml), followed by adding HONSu and DCC, each in a quantity by mol of 10 times that of amylose-glycylglycine, and agitating the mixture at room temperature overnight.

The resulting insolubles were filtered, followed by adding acetone (20 ml), agitating the mixture at 3,000 r.p.m. for 5 minutes, filtering off deposited precipitates and drying under reduced pressure to obtain activated amylose (0.4 g).

EXAMPLE 3

Preparation of Amylose-Lysozyme Hybrid

Lysozyme (11 mg) was dissolved in a 0.1M boric acid buffer (pH: 8.5), followed by adding the activated amylose (17.2 mg) obtained in Example 2 and agitating the mixture at room temperature overnight.

Figure 2:
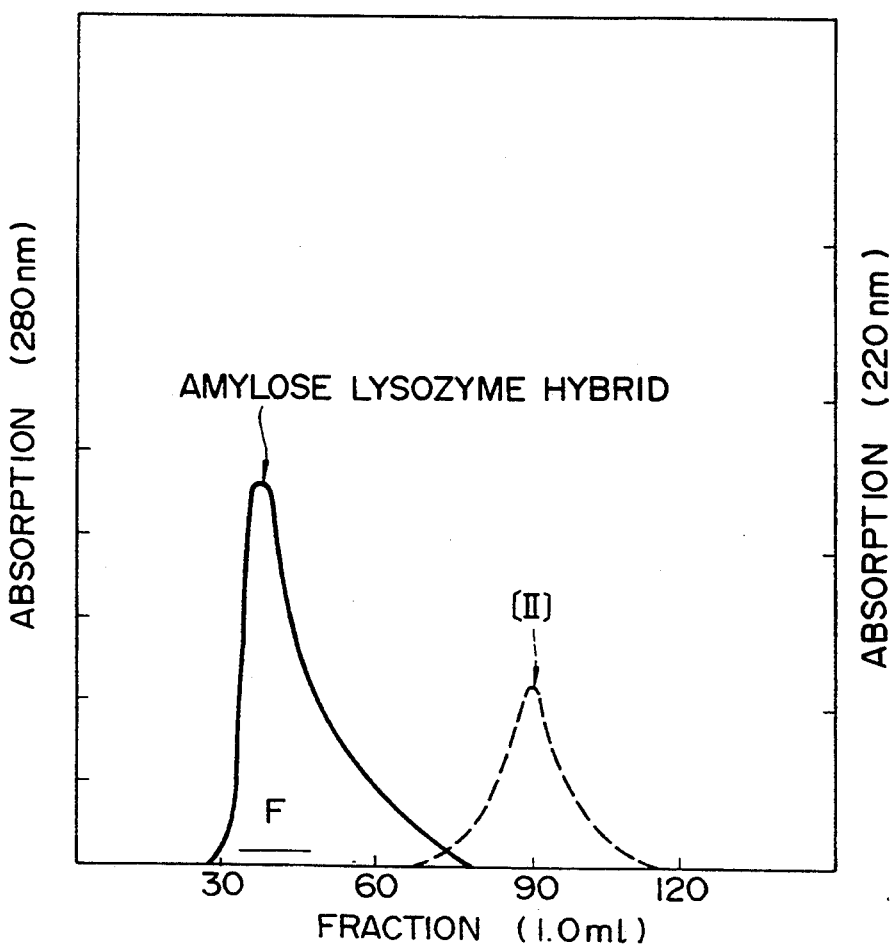

The resulting material was dialyzed with 0.1M phosphoric acid buffer (pH: 6.0) +0.1M NaCl, followed by filtering off insolubles, and subjecting the resulting filtrate to gel chromatography with a gel-filtering medium (trademark: Cellulofine GCL-300). The results are shown in FIG. 2. The former peak portion was separated. The subsequent peak portion was of unreacted activated amylose. In addition, gel filtration was carried out under the following column conditions: 1.5×64 cm, buffer: 0.1M phosphoric acid buffer+0.1% NaCl, and flow rate: 10.2 ml/hr.

The separated portion was desalted, followed by freeze-drying to obtain amylose-lysozyme hybrid (8 mg).

EXAMPLE 4

Measurement of Lysozyme Activity

Figure 3:
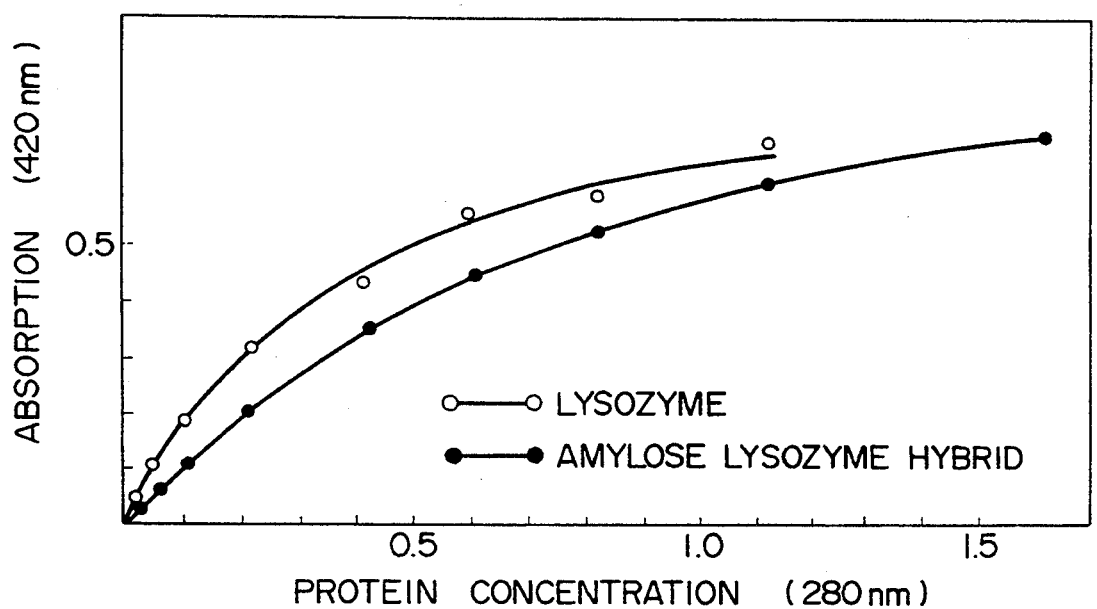

Lysozyme or amylose-lysozyme hybrid (0.1 ml) was added to a 0.1% glycol chitin solution (1 ml), followed by allowing the mixture to stand at 40° C. for 30 minutes, adding 0.05% $K_3Fe(CN)_3$ (2 ml), boiling the mixture for 15 minutes and measuring absorption at 420 mm. The relationship between the protein concentration and the absorbance is shown in FIG. 3.

EXAMPLE 5

Stability of Amylose-Lysozyme Hybrid

A lysozyme solution or an amylose-lysozyme hybrid solution (500 μl) was allowed to stand still at 20° C., 80° C., 90° C. and 100° C. for 30 minutes.

Further, it was allowed to stand at room temperature for 2.5 hours, followed by measuring its lysozyme activity according to the method of Example 4.

Figure 4:
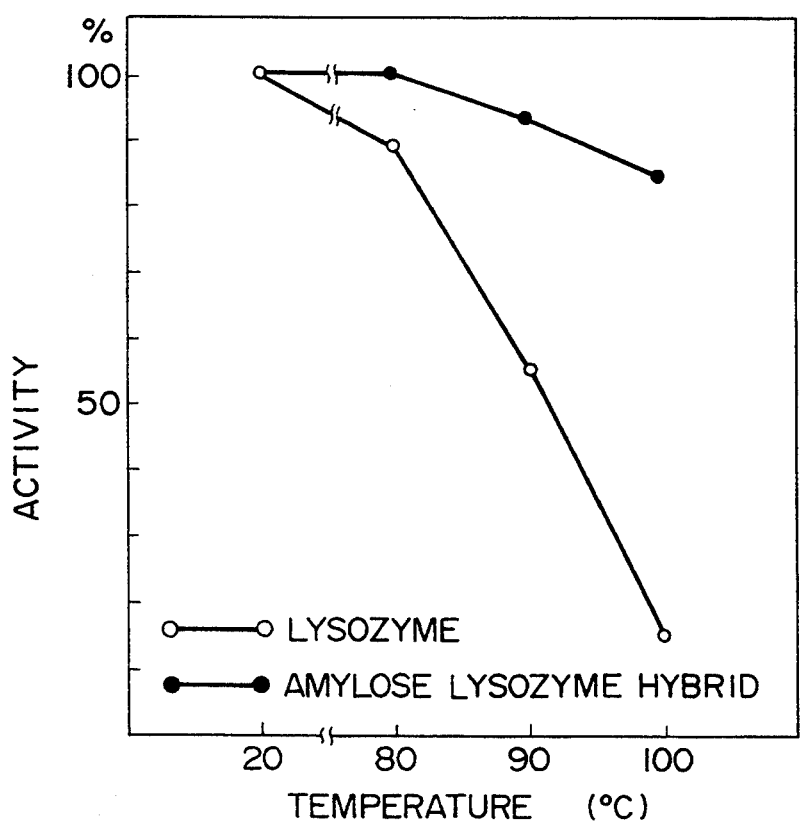

The results are shown in FIG. 4. Amylose-lysozyme hybrid retained 90% of the activity of lysozyme. As apparent from FIG. 4, at the time of treatment at 100° C. for 30 minutes, the activity of the unmodified lysozyme dropped notably, whereas the activity of amylose-lysozyme hybrid was retained at 90%, that is, the heat stability was far enhanced.

EXAMPLE 6

Preparation of Dextran-Glycylglycine

Glycylglycine (0.5 g) was dissolved in water (60 ml), followed by adding triethylamine (7 ml) and dextran (average molecular weight 10,000) (1 g) and SCBH (0.3 g) dissolved in water (40 ml), agitating the mixture at 38° C. for 4 days and subjecting the resulting reaction solution to gel filtration in the same manner as in Example 1 to obtain dextran-glycylglycine (0.85 g).

EXAMPLE 7

Preparation of Activated Dextran

Dextran-glycylglycine (0.5 g) obtained in Example 6 was dissolved in dimethylsulfoxide (5 ml), followed by adding HONSu (0.1 g) and DCC (0.15 g), agitating the mixture at room temperature overnight, filtering off insolubles, adding acetone (30 ml), agitating the mixture at 3,000 r.p.m. for 5 minutes, filtering deposited precipitates and drying under reduced pressure to obtain an activated dextran (0.35 g).

EXAMPLE 8

Preparation of Dextran-SOD Hybrid

SOD originated from *Bacillus stearothermophilus* (purchased from Biochemical Industry Co., Ltd.) (10 mg) (ca. 100,000 U) was dissolved in a 0.1M phosphoric acid buffer (pH: 7.5) (10 ml), followed by adding the activated dextran (30 mg) obtained in Example 7 and agitating the mixture at room temperature overnight.

The resulting material was dialyzed with 0.1M phosphoric acid buffer (pH: 6.0) +0.1M NaCl, followed by filtering off insolubles, subjecting the resulting filtrate to gel chromatography in the same manner as in Example 3, desalting the separated portion and freeze-drying to obtain dextran-SOD hybrid

EXAMPLE 9

Test of Dextran-SOD Hybrid Remaining in Blood

SOD or dextran-SOD hybrid prepared in Example 8, each in 1,200 U amounts, were intravenously injected into respective mouses. In the case of administration of unmodified SOD, the SOD activity level in blood after 30 minutes was nearly zero, whereas in the case of the mouse having dextran-SOD hybrid administered, the activity level was retained at 90%.

What we claim is:

1. A conjugate in essentially pure form comprising a sugar linked to a protein through a peptide linker, wherein said sugar has a reducing terminal and is free of carboxyl groups, and wherein the reducing terminal of said sugar is linked to the peptide linker.

2. A conjugate according to claim 1 wherein said sugar is dextran.

3. A conjugate according to claim 1 wherein said sugar is amylose.

4. A conjugate according to claim 1 wherein said peptide is glycylglycine.

5. A conjugate according to claim 1 wherein said sugar is a member selected from the group consisting of an aminopectin, chitosan, dextran and agarose.

6. A conjugate in essentially pure form comprising a sugar linked to an enzyme through a peptide linker, wherein said sugar has a reducing terminal and is free of carboxyl groups, and wherein the reducing terminal of said sugar is linked to the peptide linker.

7. A conjugate according to claim 6 wherein said enzyme is superoxide dismutase.

8. A conjugate according to claim 7 wherein said sugar is dextran and said peptide linkage is glycylglycine.

9. A conjugate in essentially pure form comprising a sugar linked to lysozyme through a peptide linker, wherein said sugar has a reducing terminal and is free of carboxyl groups, and wherein the reducing terminal of said sugar is linked to the peptide linker.

10. A conjugate according to claim 9, wherein said sugar is amylose.

11. A conjugate according to claim 9, wherein said peptide is glycylglycine.

12. A conjugate according to claim 9, wherein said sugar is at least one member selected from the group consisting of monosaccharides, oligosaccharides and polysaccharides.

13. A conjugate according to claim 9 wherein said sugar is a member selected from the group consisting of an aminopectin, chitosan, dextran and agarose.

14. A conjugate according to claim 9 wherein said sugar is dextran.

15. A conjugate according to claim 11 wherein said sugar is amylose.

16. A conjugate according to claim 11 wherein said sugar is dextrose.

* * * * *